United States Patent
Pham et al.

(10) Patent No.: US 10,259,760 B2
(45) Date of Patent: *Apr. 16, 2019

(54) AZEOTROPE-LIKE COMPOSITION OF 2-CHLOR0-3,3,3-TRIFLUOROPROPENE (HCFC-1233XF) AND HYDROGEN FLUORIDE (HF)

(71) Applicant: HONEYWELL INTERNATIONAL INC., Morris Plains, NJ (US)

(72) Inventors: Hang T. Pham, Amherst, NY (US); Daniel C. Merkel, Orchard Park, NY (US); Konstantin A. Pokrovski, Orchard Park, NY (US); Hsueh S. Tung, Getzville, NY (US); Rajiv R. Singh, Getzville, NY (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/289,546

(22) Filed: Oct. 10, 2016

(65) Prior Publication Data

US 2017/0183278 A1    Jun. 29, 2017

Related U.S. Application Data

(62) Division of application No. 14/022,658, filed on Sep. 10, 2013, now Pat. No. 9,464,013, which is a division
(Continued)

(51) Int. Cl.
*C11D 7/50* (2006.01)
*C07C 17/20* (2006.01)
(Continued)

(52) U.S. Cl.
CPC ............ *C07C 17/206* (2013.01); *C07C 17/38* (2013.01); *C07C 17/383* (2013.01); *C07C 21/18* (2013.01); *C11D 7/50* (2013.01); *C11D 7/5054* (2013.01)

(58) Field of Classification Search
CPC ........... C07C 19/08; C07C 31/17; C11D 7/50; C11D 7/5054
(Continued)

(56) References Cited

U.S. PATENT DOCUMENTS 6,013,846 A    1/2000   Wismer et al.
6,475,971 B2   11/2002  Pham et al.
(Continued)

FOREIGN PATENT DOCUMENTS

WO    2008/054782 A1    5/2008
WO    2008054778 A2     5/2008
(Continued)

OTHER PUBLICATIONS

Kim, et al., "A Study to Determine The Existence of an Azeotropic R-22 "Drop-In" Substitute," prepared by U.S. Department of Commerce for Electric Power Research Institute, Mar. 1996, pp. 1-45, U.S.
(Continued)

*Primary Examiner* — Gregory E Webb
(74) *Attorney, Agent, or Firm* — Fox Rothschild LLP

(57) ABSTRACT

Provided are azeotropic and azeotrope-like compositions of 2-chloro-3,3,3-trifluoropropene (HCFO-1233xf) and hydrogen fluoride (HF). Such azeotropic and azeotrope-like compositions are useful as intermediates in the production of 2,3,3,3-tetrafluoropropene (HFO-1234yf).

30 Claims, 1 Drawing Sheet

FIGURE 1: P-T-X of 1233xf/HF system

Related U.S. Application Data of application No. 12/396,528, filed on Mar. 3, 2009, now Pat. No. 8,546,624.

(60) Provisional application No. 61/034,184, filed on Mar. 6, 2008.

(51) Int. Cl.
*C07C 17/38* (2006.01)
*C07C 17/383* (2006.01)
*C07C 21/18* (2006.01)

(58) Field of Classification Search
USPC .............................. 252/67; 510/407, 408, 412
See application file for complete search history.

(56) References Cited

U.S. PATENT DOCUMENTS

| | | | |
|---|---|---|---|
| 7,795,480 | B2 | 9/2010 | Merkel et al. |
| 7,803,283 | B2 | 9/2010 | Pham et al. |
| 8,034,251 | B2 | 10/2011 | Merkel et al. |
| 8,075,797 | B2 | 12/2011 | Hulse et al. |
| 8,398,882 | B2 | 3/2013 | Rao et al. |
| 2007/0007488 | A1 | 1/2007 | Singh et al. |
| 2007/0197842 | A1 | 8/2007 | Mukhopadhyay et al. |
| 2009/0305876 | A1 | 12/2009 | Singh et al. |
| 2010/0072415 | A1* | 3/2010 | Rao .................. B01J 23/26 252/67 |
| 2010/0119460 | A1 | 5/2010 | Pham et al. |

FOREIGN PATENT DOCUMENTS

| | | |
|---|---|---|
| WO | 2008054781 A1 | 5/2008 |
| WO | 2009/003084 A1 | 12/2008 |

OTHER PUBLICATIONS

Morrison, et al., "Azeotropy in Refrigerant Mixtures," International Journal of Refrigeration, 1993, pp. 129-138, vol. 16, No. 2. U.S.

* cited by examiner

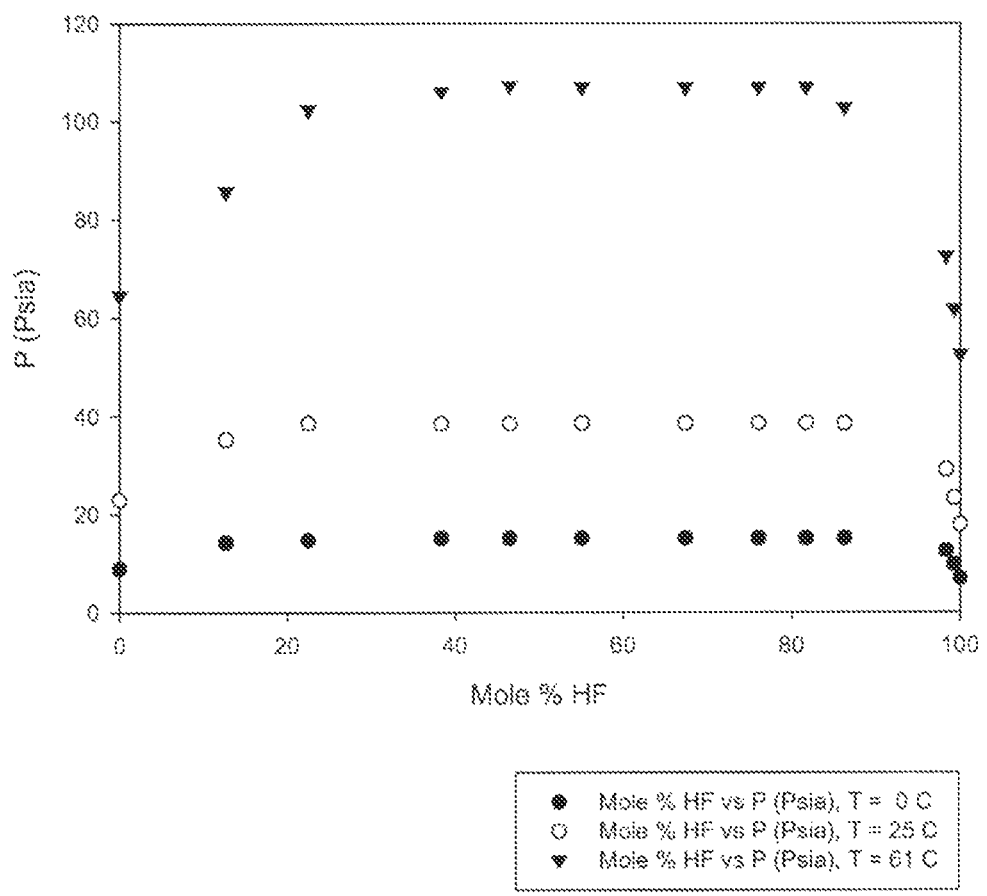
FIGURE 1: P-T-X of 1233xf/HF system

AZEOTROPE-LIKE COMPOSITION OF 2-CHLOR0-3,3,3-TRIFLUOROPROPENE (HCFC-1233XF) AND HYDROGEN FLUORIDE (HF)

CROSS REFERENCE TO RELATED APPLICATION

This application is a division of U.S. application Ser. No. 14/022,658, filed Sep. 10, 2013, which application is a division of U.S. application Ser. No. 12/396,528 filed Mar. 3, 2009 (now U.S. Pat. No. 8,546,624, issued Oct. 1, 2013), which claims the benefit of U.S. Provisional patent application No. 61/034,184, filed Mar. 6, 2008, which is incorporated herein by reference.

BACKGROUND OF THE INVENTION

Field of the Invention

The present invention pertains to azeotropic and azeotrope-like compositions of 2-chloro-3,3,3-trifluoropropene (HCFO-1233xf) and hydrogen fluoride (HF). More particularly the invention pertains to such azeotropic and azeotrope-like compositions which are useful as intermediates in the production of 2,3,3,3-tetrafluoropropene (HF0-1234yf).

Description of the Prior Art

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the Earth's ozone layer. Therefore, stratospherically safer alternatives to these materials are desirable. Consequently, there is a worldwide effort to use fluorine-substituted hydrocarbons which contain fewer or no chlorine substituents. In this regard, 2-chloro-3,3,3-trifluoropropene (HCFO-1233xf), having low ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HCF0-1233xf is an intermediate in the production of 2,3,3,3-tetrafluoropropene (HFO-1234yf) which is well known in the art as described in U.S. Applications 20070007488 and 20070197842, the specifications of which are incorporated herein by reference. HFO-1234yf has been disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid.

It has now been found that an important intermediate in the production of substantially pure HFO-1234yf, is an azeotropic or azeotrope-like composition of 2-chloro-3,3,3-trifluoropropene (HCFO-1233xf) and hydrogen fluoride. This intermediate, once formed, may thereafter be separated into its component parts by known extraction techniques. The azeotropic and azeotrope-like compositions find use not only as intermediates in the production of HFO-1234yf, but they are additionally useful as nonaqueous etchant mixtures for etching semiconductors in the electronics industry, as well as compositions for removing surface oxidation from metals. In addition, the formation of an azeotropic or azeotrope-like composition of HCFO-1233xf and hydrogen fluoride is useful in separating a mixture of HCFO-1233xf and an impurity such as a halocarbon, for example, 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane; or 1,2-dichloro-3,3,3-trifluoropropene. When it is desired to separate a mixture of HCFO-1233xf and an impurity, HF is added to form an azeotropic mixture of HCFO-1233xf and hydrogen fluoride, and then the impurity is removed from the azeotropic mixture, such as by distillation or other known means. This binary azeotrope or azeotrope-like composition is then available for separation into its component parts.

SUMMARY OF THE INVENTION

The invention provides an azeotropic or azeotrope-like composition consisting essentially of hydrogen fluoride and 2-chloro-3,3,3-trifluoropropene.

The invention further provides a method of forming an azeotropic or azeotrope-like composition which comprises forming a blend consisting essentially of from about 6.2 mole percent to about 90.7 mole percent hydrogen fluoride and from about 9.3 mole percent to about 93.8 mole percent 2-chloro-3,3,3-trifluoropropene to thereby form an azeotropic or azeotrope-like composition having a boiling point of from about 0° C. to about 61° C. at a pressure of from about 15 psia to about 107 psia.

The invention also provides a method for removing 2-chloro-3,3,3-trifluoropropene from a mixture containing 2-chloro-3,3,3-trifluoropropene and at least one impurity, which comprises adding hydrogen fluoride to the mixture in an amount sufficient to form an azeotropic or azeotrope-like composition of the 2-chloro-3,3,3-trifluoropropene and the hydrogen fluoride, and thereafter separating the azeotropic composition from the impurity.

BRIEF DESCRIPTION OF THE DRAWING

FIG. 1 shows a plot of the vapor pressures of the mixtures formed in Example 2 as measured at 0° C., 25° C. and 61° C.

DETAILED DESCRIPTION OF THE INVENTION

In a method of preparing an HCFO-1233xf precursor, reagents are fluorinated with hydrogen fluoride. This may be done, for example, by the gas phase catalytic fluorination of $CCl_2=CClCH_2Cl$ with HF to yield HCF0-1233xf. Such methods are disclosed in U.S. Application 20070197842, the specification of which is incorporated herein by reference. The reaction products of such precursors include HCFO-1233xf, unreacted HF and other by-products. Upon removal of the by-products, a binary azeotrope or azeotrope-like composition of HCFO-1233xf and HF is formed. This binary azeotrope or azeotrope-like composition is then available for separation into its component parts. The azeotropic or azeotrope-like compositions of the HCFO-1233xf and HF are also useful as recycle to the fluorination reactor. Thus, for example, in a process for producing HCFO-1233xf, one can recover a portion of the HCFO-1233xf as an azeotropic or azeotrope-like composition of HCFO-1233xf and HF and then recycle the composition to the reactor.

HCFO-1233xf forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition which comprises effective amounts of hydrogen fluoride and HCFO-1233xf to form an azeotropic or azeotrope-like composition. By effective amount is meant an amount of each component which, when combined with the other component, results in the formation of an azeotrope or azeotrope-like mixture. The inventive compositions preferably are binary azeotropes which consist essentially of combinations of only hydrogen fluoride with HCFO-1233xf.

In one embodiment, the inventive composition contains from about 6.2 mole percent to about 90.7 mole percent HF, preferably from about 53.5 mole percent to about 86.7 mole percent and most preferably from about 79.3 mole percent to about 85.3 mole percent based on the weight of the azeotropic or azeotrope-like composition. In another embodiment the inventive composition contains from about 60 mole percent to about 71 mole percent HF, preferably from about 60.2 mole percent to about 71.7 mole percent HF.

In one embodiment, the inventive composition contains from about 9.3 mole percent to about 93.8 mole percent HCFO-1233xf, preferably from about 13.3 mole percent to about 46.5 mole percent and most preferably from about 14.7 mole percent to about 20.7 mole percent based on the weight of the azeotropic or azeotrope-like composition. In another embodiment the inventive composition contains from about 29 mole percent to about 40 mole percent HCFO-1233xf, preferably from about 28.3 mole percent to about 39.8 mole percent based on the weight of the azeotropic or azeotrope-like composition.

The composition of the present invention preferably has a boiling point of about from 0° C. to about 61° C. at a pressure of about 15 psia to about 107 psia. In one embodiment it has a boiling point of about 0° C. at a pressure of about 15 psia. In another embodiment it has a boiling point of about 25° C. at a pressure of about 38 psia. In another embodiment it has a boiling point of about 61° C. at a pressure of about 107 psia. An azeotropic or azeotrope-like composition having about 82.5±1,2 mole percent HF and about 17.5±1.2 mole percent HCFO-1233xf was found at 25° C.

In another embodiment of the invention, 2-chloro-3,3,3-trifluoropropene (HCFO-1233xf) may be removed from a mixture containing 2-chloro-3,3,3-trifluoropropene (HCFO-1233xf) and an impurity which may, for example, result from manufacturing steps in the preparation of 2-chloro-3, 3,3-trifluoropropene (HCFO-1233xf). This is done by adding hydrogen fluoride to the mixture of the 2-chloro-3,3,3-trifluoropropene (HCF0-1233xf) and impurity. Hydrogen fluoride is added to the mixture in an amount sufficient to form an azeotropic composition of the 2-chloro-3,3,3-trifluoropropene (HCF0-1233xf) and the hydrogen fluoride, and thereafter the azeotropic composition is separated from the impurity, for example by distillation or other art recognized separating means. In one embodiment, the impurity itself does not form an azeotropic mixture with 2-chloro-3, 3,3-trifluoropropene (HCFO-1233xf), hydrogen fluoride or a mixture of 2-chloro-3,3,3-trifluoropropene (HCF0-1233xf) and hydrogen fluoride. In another embodiment, the impurity does form an azeotropic mixture with 2-chloro-3,3,3-trifluoropropene (HCFO-1233xf), hydrogen fluoride or a mixture of 2-chloro-3,3,3-trifluoropropene (HCF0-1233xf) and hydrogen fluoride. Typical impurities of 2-chloro-3,3,3-trifluoropropene (HCF0-1233xf) include other halocarbons which may be miscible with 2-chloro-3,3,3-trifluoropropene (HCF0-1233xf) such as 1,1,1,2,3-pentachloropropane; 1,1, 2,3-tetrachloropropene; 2,3,3,3-tetrafluoropropene; 2,3-dichloro-3,3-difluoroprop ene(HCF0-1232xf); 1,1,1,2,2-pentafluoropropane; or 1,2-dichloro-3,3,3-trifluoropropene.

The following non-limiting examples serve to illustrate the invention.

Example 1

60 g of 2-chloro-3,3,3-trifluoropropene (HCFO-1233xf) were mixed with 40 g of HF to form a heterogeneous azeotrope mixture. The vapor pressure of the mixture at about 25° C. was about 38 psia.

Example 2

Binary compositions containing solely 2-chloro-3,3,3-trifluoropropene (HCFO-1233xf) and HF were blended to form a heterogeneous azeotrope mixtures at different compositions. The vapor pressures of the mixtures were measured at about 0, 25 and 61° C. and the following results were noticed. Table 1 shows the vapor pressure measurements of HCFO-1233xf and HF as a function of composition with varying weight percent HF at constant temperatures of about 0, 25, and 61° C. The data also showed that HCFO-1233xf/HF is a heterogeneous mixture.

TABLE 1

P-T-X of HCFO-1233xf/HF

| | Pressure (Psia) | | |
|---|---|---|---|
| Mole % HF | T = 0° C. | T = 25° C. | T = 61° C. |
| 0.00 | 8.87 | 22.88 | 64.58 |
| 12.70 | 14.21 | 35.2 | 85.62 |
| 22.50 | 14.69 | 38.48 | 102.4 |
| 38.34 | 15.03 | 38.4 | 106.08 |
| 46.46 | 15.03 | 38.35 | 107.34 |
| 55.06 | 15.03 | 38.45 | 106.95 |
| 67.39 | 15.03 | 38.45 | 106.95 |
| 76.06 | 15.03 | 38.45 | 107 |
| 81.72 | 15.03 | 38.45 | 107.05 |
| 86.27 | 15.08 | 38.4 | 102.88 |
| 98.36 | 12.51 | 29.04 | 72.53 |
| 99.30 | 9.7 | 23.17 | 61.72 |
| 100.00 | 6.87 | 17.82 | 52.43 |

The data also shows that the mixture is azeotropic or azeotrope-like since the vapor pressure of the mixtures of HCFO-1233xf and HF is higher, at all indicated blend proportions, than vapor pressures of HCFO-1233xf and HF alone, i.e. as indicated in the first and last rows of Table 1 when HF is 0.0 mole % and HCFO-1233xf is at 100.0 mole % as well as when HCFO-1233xf is at 0.0 mole % and HF is at 100.0 mole %. The data from Table 1 is shown in graphic form in FIG. 1.

Example 3

The azeotropic or azeotrope-like composition of the HCF0-1233xf/HF mixture was also verified by Vapor-Liquid-Liquid equilibrium (VLLE) experiment. 63.5 g of 2-chloro-3,3,3-trifluoropropene (HCFO-1233xf) were mixed with 36.5 g of HF to form a heterogeneous mixture (visual observation) at 24° C. The vapor composition, upper liquid (HF rich), and bottom liquid (organic) were sampled. The result shows that the azeotropic composition is about 82.5±1.2 mole percent HF at 24° C.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. An azeotropic or azeotrope-like composition which consists essentially of from about 6.2 mole percent to about 90.7 mole percent hydrogen fluoride and from about 9.3 mole percent to about 93.8 mole percent 2-chloro-3,3,3-trifluoropropene, which composition has a boiling point of from about 0° C. to about 61° C. at a pressure of from about 15 psia to about 107 psia.

2. The composition of claim 1 which consists of hydrogen fluoride and 2-chloro-3,3,3-trifluoropropene.

3. The composition of claim 1 wherein the hydrogen fluoride is present in the amount from about 53.5 mole percent to about 86.7 mole percent.

4. The composition of claim 1 wherein the hydrogen fluoride is present in the amount from about 79.3 mole percent to about 85.3 mole percent.

5. The composition of claim 1 wherein the hydrogen fluoride is present in the amount from about 60 mole percent to about 71 mole percent.

6. The composition of claim 1 wherein the hydrogen fluoride is present in the amount from about 60.2 mole percent to about 71.7 mole percent.

7. The composition of claim 1 wherein the 2-chloro-3,3,3-trifluoropropene is present in the amount from about 13.3 mole percent to about 46.5 mole percent.

8. The composition of claim 1 wherein the 2-chloro-3,3,3-trifluoropropene is present in the amount from about 14.7 mole percent to about 20.7 mole percent.

9. The composition of claim 1 wherein the 2-chloro-3,3,3-trifluoropropene is present in the amount from about 29 mole percent to about 40 mole percent.

10. The composition of claim 1 wherein the 2-chloro-3,3,3-trifluoropropene is present in the amount from about 28.3 mole percent to about 39.8 mole percent.

11. The composition of claim 1 having a boiling point of about 0° C. at a pressure of about 15 psia; or a boiling point of about 25° C. at a pressure of about 38 psia; or a boiling point of about 61° C. at a pressure of about 107 psia.

12. A method of forming an azeotropic or azeotrope-like composition which comprises forming a blend consisting essentially of from about 6.2 mole percent to about 90.7 mole percent hydrogen fluoride and from about 9.3 mole percent to about 93.8 mole percent 2-chloro-3,3,3-trifluoropropene to thereby form an azeotropic or azeotrope-like composition having a boiling point of from about 0° C. to about 61° C. at a pressure of from about 15 psia to about 107 psia.

13. The method of claim 12 wherein the composition consists of hydrogen fluoride and 2-chloro-3,3,3-trifluoropropene.

14. The method of claim 12 wherein the hydrogen fluoride in present in an amount of from about 15 to about 50 weight percent.

15. The method of claim 12 wherein the 2-chloro-3,3,3-trifluoropropene is present in the amount from about 50 to about 85 weight percent.

16. The method of claim 12 wherein the composition has a boiling point of about 0° C. at a pressure of about 15 psia; or a boiling point of from about 25° C. at a pressure of about 38 psia; or a boiling point of about 61° C. at a pressure of about 107 psia.

17. The method of claim 12 further comprising the step of separating 2-chloro-3,3,3-trifluoropropene from an azeotropic or azeotrope-like composition of 2-chloro-3,3,3-trifluoropropene and hydrogen fluoride using pressure swing distillation.

18. The method of claim 12 further comprising the step of feeding the azeotropic or azeotrope-like composition of 2-chloro-3,3,3-trifluoropropene and hydrogen fluoride to a fluorination reactor as a source of hydrogen fluoride.

19. A method for removing 2-chloro-3,3,3-trifluoropropene from a mixture containing 2-chloro-3,3,3-trifluoropropene and at least one impurity, which comprises adding hydrogen fluoride to the mixture in an amount sufficient to form an azeotropic or azeotrope-like composition of the 2-chloro-3,3,3-trifluoropropene and the hydrogen fluoride, and thereafter separating the azeotropic composition from the impurity.

20. The method of claim 19 wherein the impurity does not form an azeotropic mixture with 2-chloro-3,3,3-trifluoropropene, hydrogen fluoride or a mixture of 2-chloro-3,3,3-trifluoropropene and hydrogen fluoride.

21. The method of claim 19 wherein the impurity does form an azeotropic mixture with 2-chloro-3,3,3-trifluoropropene, hydrogen fluoride or a mixture of 2-chloro-3,3,3-trifluoropropene and hydrogen fluoride.

22. The process of claim 19 wherein the impurity comprises a halocarbon.

23. The method of claim 19 wherein the impurity is miscible with 2-chloro-3,3,3-trifluoropropene.

24. The method of claim 19 wherein the impurity comprises one more of 1,1,1,2,3-pentachloropropane; 1,1,2,3-tetrachloropropene; 2,3,3,3-tetrafluoropropene; 2,3-dichloro-3,3-difluoropropene; 1,1,1,2,2-pentafluoropropane and 1,2-dichloro-3,3,3-trifluoropropene.

25. The method of claim 19 wherein the separating is conducted by distillation.

26. The method of claim 19 wherein the azeotropic composition consists essentially of from about 6.2 mole percent to about 90.7 mole percent hydrogen fluoride and from about 9.3 mole percent to about 93.8 mole percent 2-chloro-3,3,3-trifluoropropene.

27. The method of claim 19 wherein the azeotropic composition consists essentially of from about 53.5 mole percent to about 86.7 mole percent hydrogen fluoride and from about 13.3 mole percent to about 46.5 mole percent 2-chloro-3,3,3-trifluoropropene.

28. The method of claim 19 wherein the azeotropic composition consists essentially of from about 79.3 mole percent to about 85.3 mole percent hydrogen fluoride and from about 14.7 mole percent to about 20.7 mole percent 2-chloro-3,3,3-trifluoropropene.

29. The method of claim 19 wherein the azeotropic composition consists essentially of from about 60 mole percent to about 71 mole percent mole percent hydrogen fluoride and from about 29 mole percent to about 40 mole percent 2-chloro-3,3,3-trifluoropropene.

30. The method of claim 19 wherein the azeotropic composition consists essentially of from about 60.2 mole percent to about 71.7 mole percent hydrogen fluoride and from about 28.3 mole percent to about 39.8 mole percent 2-chloro-3,3,3-trifluoropropene.

* * * * *